(12) United States Patent
Hughes et al.

(10) Patent No.: US 6,197,499 B1
(45) Date of Patent: Mar. 6, 2001

(54) METHOD FOR THE FLUORESCENT DETECTION OF A DNA SEQUENCE IN REAL TIME

(75) Inventors: Stephen H. Hughes, Smithsburg; Ramesh Kumar, Frederick, both of MD (US); John Brumbaugh, Lincoln, NE (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 07/920,013

(22) Filed: Jul. 27, 1992

Related U.S. Application Data

(63) Continuation of application No. 07/484,573, filed on Feb. 26, 1990, now abandoned.

(51) Int. Cl.$^7$ ............................. C12Q 1/68; C07H 21/04

(52) U.S. Cl. ........................... 435/6; 435/91.1; 536/24.3; 935/77; 935/78

(58) Field of Search .................................. 435/6; 935/77, 935/78; 536/24.33, 24.3

(56) References Cited

U.S. PATENT DOCUMENTS 4,683,202  7/1987  Mullis ................................ 435/91.1

OTHER PUBLICATIONS

Kumar et al., A Method For The Rapid Screening Of Human Blood Samples For The Presence Of HIV–1 Sequences: The Probe–Shift Assay, Aids Research and Human Retroviruses, 1989, vol. 5, No. 3, pp. 345–354.

Siegler, N., DNA–Based Testing: A Progress Report, ASM News, 1989, vol. 55, No. 6, pp. 308–312.

Wu et al. Allele–Specific Enzymatic Amplification of B–Globin Genomic DNA For Diagnosis Of Sickle Cell Anemia, Proceedings of the National Academy of Sciences, Apr. 1989, vol. 86, pp. 2757–2760.

Brumbaugh et al., Continuous, On–Line DNA Sequencing Using Oligodeoxynucleotide Primers With Multiple Fluorophores, Proceedings of the National Academy of Sciences, Aug. 1988, vol. 85, pp. 5610–5614.

Gebeyechu et al. Novel Biotinylated Nucleotide—Analogs For Labeling and Colorimetric Detection Of DNA, Nucleic Acids Research, 1987, vol. 15, Issue 11, pp. 4513–4534.

Saiki et al., Enzymatic Amplification of B–Globin Genomic Sequences and Restriction Site Analysis for Diagnosis of Sickel Cell Anemia, Science, 1985, vol. 230, pp. 1350–1354.

Landegren, Ulf et al. "A Ligase–Mediated Gene Detection Technique" Science (1988) 241:1077–1080.

Gyllensten et al., PNAS, vol. 85, pp. 7652–7656, Oct. 1988.*

* cited by examiner

*Primary Examiner*—George C. Elliott
*Assistant Examiner*—Andrew Wang
(74) *Attorney, Agent, or Firm*—Morgan & Finnegan, L.L.P.; William S. Feiler; Dorothy R. Auth

(57) ABSTRACT

The present invention relates to a method of detecting a DNA sequence by means of a DNA:DNA hybrid in real time using fluorescence. The present invention eliminates the need to use radioactive probes to detect the DNA and eliminates the delay needed for autoradiographic exposure of the X-ray to the radioactive label.

10 Claims, 3 Drawing Sheets

METHOD FOR THE FLUORESCENT DETECTION OF A DNA SEQUENCE IN REAL TIME

This is a continuation of application Ser. No. 07/484,573, filed on Feb. 26, 1990, now abandoned.

BACKGROUND OF THE INVENTION

1. Field of the Invention

The present invention relates to the detection of a DNA sequence in real time using fluorescence.

2. Background Information

The polymerase chain reaction (PCR) developed by Saiki et al. [Science 230, 1350–1354 (1985)] provided a method for rapidly amplifying small specific segments of DNA. The PCR technique has greatly simplified the analysis of DNA sequences at the genomic level.

Detection or identification of a segment of DNA involves a two step procedure. The first step is the PCR amplification reaction using carefully selected primers. The second step identifies whether the desired DNA segment was amplified.

Prior to the present invention, the second step has required the use of a radioactively labeled DNA probe to precisely identify a PCR amplified DNA segment. There are several disadvantages associated with the use of a radioactively labeled probe. For example, radioactive probes are dangerous to handle and when labeled with $^{32}P$, which is the standard protocol, the probe has a short useful life (a few weeks at most). In addition, the use of a radioactive probe prevents detection of the results in real time, that is, a delay for an autoradiographic exposure time is required.

SUMMARY OF THE INVENTION

Accordingly, it is an object of the present invention to provide a method for detecting an amplified DNA sequence without the use of a radioactive probe.

It is another object of the present invention to provide a method for detecting an amplified DNA sequence in real time.

In one embodiment the present invention relates to a method of detecting a DNA sequence by means of a fluorescent DNA:DNA hybrid comprising the steps of:
  i) asymmetrically amplifying said DNA sequence;
  ii) hybridizing a fluorescently labeled probe complementary to a segment of the amplified DNA sequence to the amplified DNA wherein the hybridization is effected in solution;
  iii) separating the hybridized probe from the unhybridized probe by electrophoresis; and
  iv) detecting during electrophoresis the presence or absence of a DNA:probe hybrid by fluorescence detection.

In another embodiment the present invention relates to a method of screening a sample for a pathogen comprising the steps of:
  i) asymmetrically amplifying a DNA sequence unique to said pathogen;
  ii) hybridizing a fluorescently labeled probe complementary to a segment of the amplified DNA sequence to the amplified DNA sequence wherein the hybridization is effected in solution;
  iii) separating the hybridized probe from the unhybridized probe by electrophoresis; and
  iv) detecting during electrophoresis the presence or absence of a DNA:probe hybrid by detection of the fluorescent label.

In a further embodiment the present invention relates to a method of simultaneously screening a sample for the presence of several pathogens comprising the steps of:
  i) asymmetrically amplifying a DNA sequence unique to each pathogen whose presence or absence is being determined;
  ii) hybridizing a fluorescently labeled probe for each pathogen being detected complementary to a segment of the pathogen's amplified DNA sequence to the amplified DNA wherein the hybridization is effected in solution;
  iii) separating the sample by electrophoresis; and
  iv) detecting during electrophoresis by a laser scanner-imaging device the presence or absence of a DNA: probe hybrid for each pathogen by detection of the fluorescent label.

Various other objects and advantages of the present invention will become obvious from the drawings and the following description of the invention.

DETAILED DESCRIPTION OF THE INVENTION

Figure 1:
FIGS. 1, 2 and 3 show a montage of computer screens from 3 runs illustrating typical results obtained with the method of the present invention. A variety of samples and treatments were used. Of particular note are the bands with arrows or the designation **. These show HIV positive sequences which have been detected.
Figure 2:
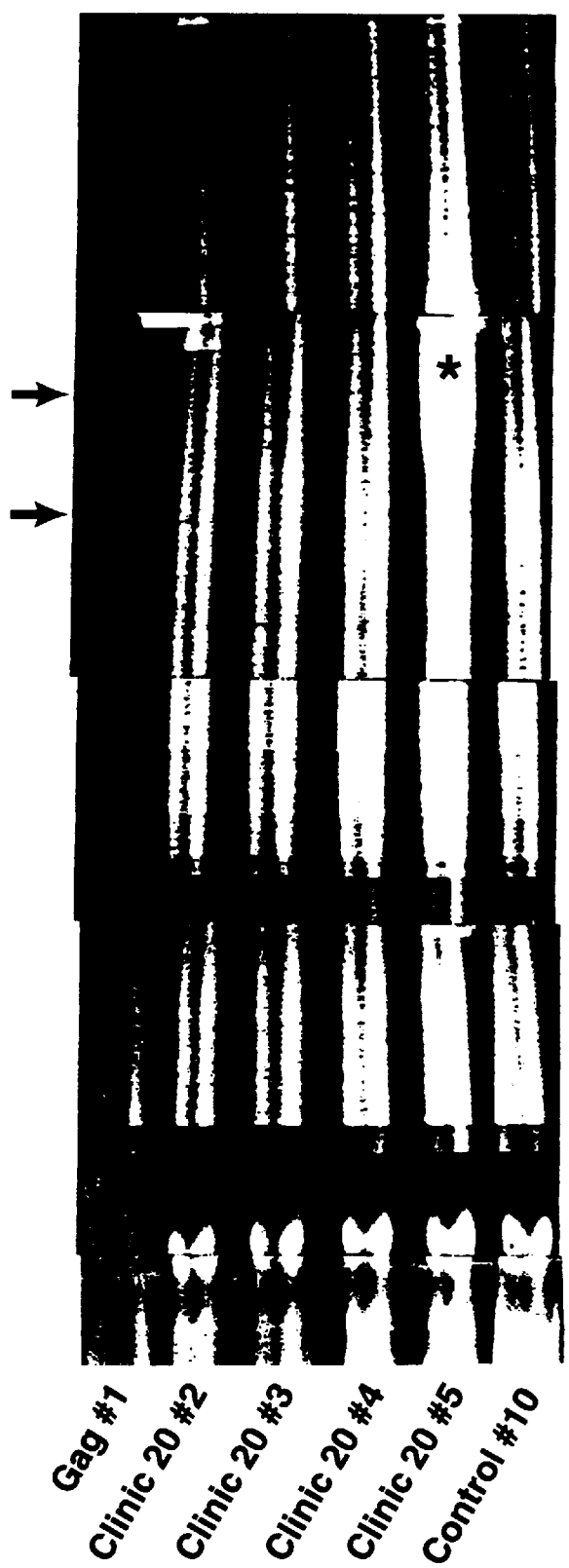
Figure 3:
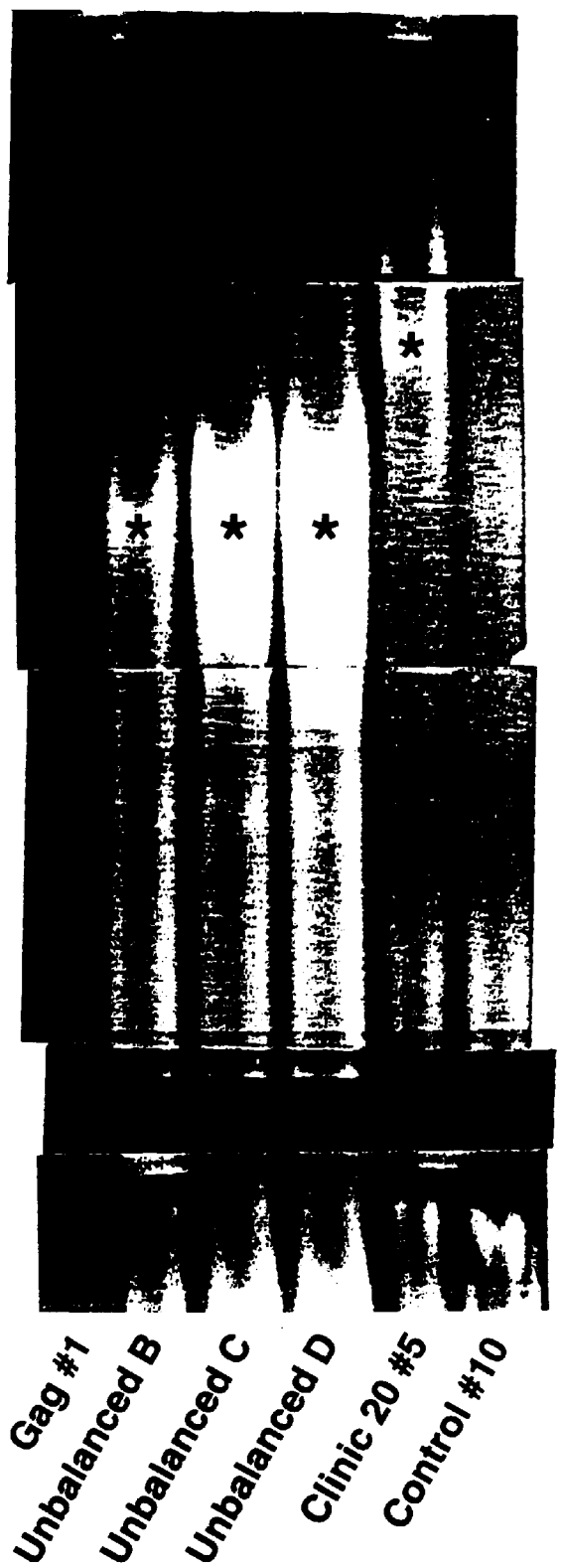

The present invention relates to a method of detecting a DNA sequence by means of a DNA:DNA hybrid in real time using fluorescence.

In the method of the present invention, a specific DNA sequence is amplified and then the presence or absence of the amplified sequence is detected in real time with fluorescence. The DNA may be purified before being amplified. A DNA sequence is asymmetrically amplified by conventional PCR techniques such as those described by Gyllensten et al, [PNAS (U.S.A.) 85, 7652–7656 (1985)]. Symmetrical amplification results in the production of an equal number of + and − strands. With asymmetrical amplification, equal numbers of + and − DNA strands, are not created. Asymmetrical amplification is achieved using an excess of one of the paired primers usually in a ratio of between 10:1 and 100:1, preferably 50:1. The ratio to be used depends on the sequence to be detected but is easily determined by one skilled in the art. While amplification of both single strands occurs more DNA strands primed from the abundant primer are produced.

Asymmetrical amplification is necessary because detection of fluorescence is less sensitive than detection of radioactivity. Therefore, naturally occurring competition between the complementary strand and the labeled probe for the DNA sequence must be reduced. Excess production of the one DNA strand encoding the sequence to be detected results in the needed reduction in competition and allows for detection of its presence with fluorescence.

After amplification, the denatured DNA sample is mixed in solution with a fluorescently labeled probe and hybridization of the probe to the desired DNA sequence occurs. Preferably, the probe is complementary to a region in the center of the amplified sequence. The probe is labeled with a fluorescent group such as fluorescein isothiocyanate or tetramethyl rhodamine [Brumbaugh et al., PNAS (U.S.A.)

85, 5610–5614 (1988); Ruth et al., DNA 4, 93 (1985); Jablonski et al., Nucleic Acids Res. 14(15), 6115–6128 (1986); and Ruth, DNA 3, 123 (1984)].

The sample containing the amplified DNA and the fluorescent probe is then electrophoresed, advantageously on a polyacrylamide gel, which is scanned in real time during the electrophoretic run. In a preferred embodiment, a laser scanner-imaging device is used. Since the size and geometry of the molecule affect the speed with which it migrates through the gel, the labeled probe and labeled probe:DNA hybrid run at different rates which separates the free probe from the hybridized probe and enables the detecting device, preferably a laser scanner-imaging device, to detect separate bands on the gel by excitation of the fluorescent probe.

The detecting device comprises a bright focused light source of a particular wavelength, such as that supplied by a laser, which excites the fluorescent label on the probe as the migrating band passes the light source during the electrophoretic run and a reader, such as a photocell, which detects the emissions given off by the excited fluorescent probe as the migrating band passes the reader. The device may further comprise a computer coupled to the reader which records the data as it is received. Laser scanner-imaging devices suitable for use in the present method include, but are not limited to fluorescent DNA sequencing machines such as those made by Dupont de Nemours, Applied Biosystems, and preferably the sequencing machine by Li-Cor, Inc. described in PNAS U.S.A. 85, pp. 5610–5614, (1988).

In the presence of its complementary DNA sequence, the fluorescent probe hybridizes thereto causing an alteration in the migration of the probe which is detected by the reader. The shift in migration results in a change in the length of time required for the probe to be driven past the reader. Accordingly, the first fluorescent signal to pass the detector is unhybridized probe. The second signal is a "common band" present in nearly all samples. The third band, if present, represents the amplified DNA:probe hybrid. Detection of the presence of the amplified DNA sequence is in real time since time for autoradiographic exposure is not required.

A decrease in the number of false negatives is obtained by initial purification of the DNA followed by booster PCR [Amplifications, Issue 3 (Sept. 1989) pp. 12–13, (1989)] before asymmetrical amplification is carried out. The DNA is purified from the sample by techniques known in the art.

The term "in real time" as used herein means no delay between the time of the electrophoretic run and the time the results are available.

The present invention can be used for early detection of, for example, pathogens such as herpes, syphilis, hepatitis and HTLV, particularly HIV. It can also be used to detect oncogene sequences before development of neoplasms and to detect genetic diseases. Probes suitable for use in such detection methods can be easily chosen by one skilled in the art. The probe used will depend on the pathogen whose presence or absence is being detected.

In a preferred embodiment, the method of the present invention is able to distinguish between HIV infected and uninfected samples prepared in the laboratory. The present invention also can be used to detect the presence of an HIV DNA sequence in samples taken from patients.

In one embodiment, the present invention relates to simultaneous screening of a sample, such as a blood sample, for the presence of several pathogens. The simultaneous screen can be conducted, for example, by screening the sample with several probes of differing sizes each specific for a different pathogen. In this case, the presence of each pathogen in the sample results in a unique band of hybrid DNA:probe which migrates at a unique rate due to the difference in the probe sizes. Each hybrid band can be detected by, for example, a laser scanner-imaging device and can be distinguished from other hybrid bands by its rate of migration.

Screening the sample with several probes each labeled with a fluorescent group of a different color also permits the detection of several pathogens in a sample. In this instance, the laser scanner-imaging device must be able to detect different colored fluorescent groups. The presence of each DNA:probe hybrid band labeled with fluorescent groups of differing colors can be detected and distinguished from each other by, for example, a laser scanner-imaging device as the hybrid bands migrate through the electrophoretic medium.

For purposes of illustrating a preferred embodiment of the present invention, in the following non-limiting example, HIV DNA present in cells was amplified and then detected using a fluorescent probe. It is, however, to be understood that the discussion generally applies to the detection of other DNA sequences.

EXAMPLE

Cell Lysates

Samples were prepared as previously described [Kumar et al., AIDS Research and Human Retroviruses 5, 345–353 (1989)]. Clinical samples and HIV-1 and human T cell leukemia virus (HTLV-1) infected cells were handled in a Biological Safety level 3 laboratory following NIH safety guidelines. The T lymphocyte cell line H9 was used as a negative control in some experiments. Most clinical samples were peripheral blood mononuclear cells, separated from heparinized blood samples. The cells were viably cryopreserved in a controlled-rate freezer and stored at −70° C. DNA substrates for PCR analysis were prepared by washing cells in phosphate-buffered saline (PBS), pH 7.5, three times, followed by suspending the cells in cold distilled water at the desired concentration. For the PCR reaction the cells were suspended at $1$–$5 \times 10^6$ cells per ml. Cells were lysed, and virus was inactivated by heating at 95° C. for 20 minutes. Lysates were stored at −20° C.

DNA Purification and Booster PCR

Though not necessary for the detection of the presence or absence of the DNA sequence, purification of the DNA and booster PCR prior to asymmetrical amplification can result in a decrease in the number of false positives. Purification alone also results in some reduction in the number of false positives.

The DNA was purified by phenol extraction followed by ethanol precipitation as previously described [Maniatis et al., 1982. Molecular Cloning: A Laboratory Manual, Cold Spring Harbor Laboratory, NY].

Booster PCR was performed to enhance the specificy of the yield [Amplifications, Issue 3, pp.12–13, Sept.1989]. The purified DNA was amplified using a $10^7$ fold molar excess of primers with respect to the expected amount of the HIV sequence to be amplified. 15 to 20 cycles were carried out using the excess primers.

Polymerase Chain Reaction

PCR was performed essentially as previously described [Saiki et al., Science 239, 487–491 (1988) and Saiki et al., Science 230, 1350–1354 (1985) and U.S. Pat. Nos. 4,683,202 and 4,683,195]. A commercially available reagent kit (Perkin Elmer-Cetus) was used. Amplifications were performed in a total volume of 200 $\mu$l containing 30 $\mu$l cell lysates (up to $5 \times 10^5$ cells) and 2 $\mu$l (5 units) Taq DNA polymerase. All primers were gel purified and resuspended in distilled water at 100 µg/ml. Asymmetric amplification was carried out using a 50:1 ratio of paired primers resulting in an excess of the strand primed from the more abundant primer. The samples were subjected to denaturation for 1 minute at 94° C., annealing at 52° C. for 2 minutes, and polymerization at 72° C. for 3 minutes during each cycle. A total of 35 cycles of PCR were performed in a thermal DNA cycler machine (Perkin Elmer-Cetus). Amplified samples were stored at −20° C.

Probe-Shift Assay

The presence of the amplified HIV sequences were unambiguously identified by hybridization with an oligonucleotide that matches the middle of the correctly amplified sequence. HIV sequences were detected by a liquid hybridization-gel retardation assay [Kumar et al., Oncogene 3, 647–651 (1988)]. 10 µl of the DNA sample was mixed with 6 µl of a fluorescently labeled probe in a 25 µl final reaction volume containing 0.75 M NaCl. One probe used was 20 bases long and doubly labeled with 2 fluoresceins at the position of two thymidines. The other probe used was 32 bases long with 2 fluoresceins at internal thymidine sites. The amplified regions and both probes were from a region of the GAG gene of HIV.

Reactions, overlaid with paraffin oil, were heated at 97° C. for 10 min. to denature the DNA, and then rapidly cooled to 79° C. optimal annealing temperature for hybridization in a thermal DNA Cycler (Perkin Elmer-Cetus). Hybridization was carried out for 2 hours and terminated by cooling on ice. Each sample was then loaded into a well of a 6% non-denaturing acrylamide gel and electrophoresed.

Fluorescent Detection

The electrophoretic apparatus was scanned in real time using a sequencing laser scanner-imaging device by Li-Cor, Inc.

The first fluorescent signal to pass the detector was unhybridized probe. The second signal was a "common band" present in nearly all samples. The third band or signal, if present, represented the amplified DNA segment of interest.

All references cited hereinabove are hereby incorporated by reference.

It is understood that the examples and embodiments described herein are for illustrative purposes only and that various modifications or changes in light thereof will be suggested to one skilled in the art and are to be included in the spirit and purview of this application and scope of the claims.

What is claimed is:

1. A method for detecting a DNA sequence comprising the steps of:
    i) asymmetrically amplifying the DNA sequence so that one strand of the DNA sequence is amplified to a greater extent than the strands' complement forming an amplified DNA strand;
    ii) hybridizing a fluorescently labeled probe to the amplified DNA strand wherein said fluorescently labeled probe is complementary to a segment of the amplified DNA strand, the hybridization being effected in solution and forming a fluorescently labeled hybridized probe;
    iii) separating the fluorescently labeled hybridized probe from unhybridized labeled probe by electrophoresis; and
    iv) detecting during electrophoresis the presence or absence of the fluorescently labeled hybridized probe by fluorescence detection, wherein the presence of the fluorescently labeled hybridized probe indicates the presence of said DNA sequence.

2. The method according to claim 1 further comprising prior to step i) the steps of:
    i) purifying DNA from a sample; and
    ii) amplifying said DNA sequence in the presence of about a $10^7$ fold molar primer excess.

3. The method according to claim 1 wherein said DNA:probe hybrid is detected with a laser scanner-imaging device.

4. The method according to claim 1 wherein said probe is labeled with fluorescein.

5. A method of screening a sample for a pathogen comprising the steps of:
    i) asymmetrically amplifying a DNA sequence unique to said pathogen;
    ii) hybridizing a fluorescently labeled probe complementary to a segment of the amplified DNA to the amplified DNA sequence wherein the hybridization is effected in solution;
    iii) separating the hybridized probe from the unhybridized probe by electrophoresis; and
    iv) detecting during electrophoresis the presence or absence of a DNA:probe hybrid by detection of the fluorescent label, wherein the presence of the hybrid indicating the presence of said pathogen.

6. A method according to claim 5 wherein said pathogen is HIV.

7. The method according to claim 5 wherein said sample is blood.

8. A method of simultaneously screening a sample for the presence of several pathogens comprising the steps of:
    i) asymmetrically amplifying a DNA sequence unique to each pathogen whose presence or absence is being determined;
    ii) hybridizing fluorescently labeled probes to the amplified DNA in solution;
    iii) separating the sample by electrophoresis; and
    iv) detecting during electrophoresis by a laser scanner-imaging device the presence or absence of a DNA:probe hybrid for each pathogen by detection of the fluorescent label, wherein the presence of the hybrid indicating the presence of one or more pathogens in said sample.

9. The method according to claim 8 wherein each probe is labeled with a different colored fluorescent group and are thereby distinguishable by the laser scanner-imaging device.

10. The method according to claim 8 wherein each probe is a different size and is thereby distinguishable by the laser scanner-imaging device.

* * * * *